United States Patent [19]

Presnall

[11] Patent Number: 4,868,336
[45] Date of Patent: Sep. 19, 1989

[54] MANUFACTURE OF DISULFIDES

[75] Inventor: Stewart H. Presnall, Borger, Tex.

[73] Assignee: Phillips Petroleum Company, Bartlesville, Okla.

[21] Appl. No.: 123,089

[22] Filed: Nov. 20, 1987

[51] Int. Cl.$^4$ .................................. C07C 148/00
[52] U.S. Cl. .................................. 568/25; 568/26
[58] Field of Search ............... 568/25, 26; 548/158

[56] References Cited

U.S. PATENT DOCUMENTS

| | | | |
|---|---|---|---|
| 2,503,644 | 4/1950 | Warner et al. | 568/26 |
| 2,539,808 | 1/1951 | Brooner | 568/26 |
| 2,656,392 | 10/1953 | Schulze et al. | 568/26 |
| 2,790,008 | 4/1957 | Warner | 568/26 |
| 2,839,581 | 6/1958 | Warner | 568/26 |
| 2,979,532 | 4/1961 | MacGregor | 568/26 |
| 3,004,071 | 10/1961 | Warner et al. | 568/26 |
| 3,340,324 | 9/1967 | Warner | 568/26 |
| 3,565,959 | 2/1971 | Takase et al. | 568/26 |
| 4,307,236 | 12/1981 | Zengel et al. | 548/186 |
| 4,558,135 | 12/1985 | Zengel et al. | 548/158 |

Primary Examiner—Mary E. Ceperley
Attorney, Agent, or Firm—Lynda S. Jolly

[57] ABSTRACT

A method for preparing disulfides comprising combining at least one mercaptan of the general formula R-SH wherein R is selected from the group consisting of an alkyl, aryl, aralkyl, cycloalkyl, arylcycloalkyl radical, and mixtures thereof; at least one oxidizing agent; at least one aqueous base; at least one oxygen containing water miscible organic compound; and at least one divalent transition metal carboxylic acid salt and/or divalent transition metal sulfate salt.

21 Claims, No Drawings

MANUFACTURE OF DISULFIDES

BACKGROUND OF THE INVENTION

This invention relates to a method for making organic disulfides.

It is known in the art to use a variety of methods to oxidize compounds having the general formula RSH, also known as thiols or mercaptans, to the corresponding disulfide according to the equation: $2R\text{-}SH + \frac{1}{2}O_2 \rightarrow R_2S_2 + H_2O$. Unfortunately, each known process has its limitations. One method, adapted from the crude oil sweetening process, is thiol oxidation in the presence of copper chloride. The thiol is oxidized in an acidic solution of copper chloride dissolved in a methyl carbitol. This method is relatively expensive and extremely corrosive. Another thiol oxidation process, which is less corrosive, utilizes elemental sulfur. However, since unwanted trisulfides are also produced, only low molecular weight thiols can be oxidized. In yet another thiol oxidation process, which is used for sweetening crude oil, organo-metallo complexes are used to oxidize thiols to disulfides. This process is for primarily low molecular weight thiols and does not result in complete thiol oxidation, as represented by a high final mercaptan sulfur content.

High molecular weight disulfides are used as an additive in the plastics industry as a chain transfer agent in polymerization processes. Furthermore, high purity disulfides are preferred so as not to impart any undesirable color to the end product. Therefore, a non-corrosive process to efficiently produce relatively pure high molecular weight disulfides is desired.

SUMMARY OF THE INVENTION

It is an object of this invention to provide a novel process for the oxidation of compounds having the general formula RSH to the corresponding disulfide.

It is a further object of this invention to provide a relatively non-corrosive process for the oxidation of RSH compounds to the corresponding disulfide.

It is yet another object of this invention to provide a process for the oxidation of high molecular weight RSH compounds to the corresponding disulfide.

It is yet a further object of this invention to provide a process for the oxidation of RSH compounds to the corresponding, easily purified disulfide.

In accordance with this invention, thiols, of the formula R-SH wherein R is selected from the group consisting of alkyl, aryl, aralkyl, alkaryl, cycloalkyl, arylcycloalkyl radicals, and mixtures thereof, are oxidized to the corresponding disulfide(s) in the presence of: an oxidizing agent; an aqueous base sufficient to give a pH within the range of about 8 to about 14; an oxygen-containing, water-miscible organic compound; and a divalent transition metal catalyst selected from the group consisting of divalent transition metal carboxylic acid salts, divalent transition metal carboxylic acid derivative salts, divalent transition metal sulfate, salts, and mixtures thereof.

DESCRIPTION OF THE PREFERRED EMBODIMENTS

Reactants

The mercaptan compounds which are suitable for oxidation by the process of this invention have the general formula RSH wherein R is an aryl, alkyl, alkaryl aralkyl, cycloalkyl, or arylcycloalkyl radical. Preferably, the aryl, alkyl, alkaryl, aralkyl, cycloalkyl, or arylcycloalkyl radical contains about 8 to about 18, most preferably about 10 to about 16 carbon atoms. Thiols with less than about 8 carbon atoms, if oxidized according to this invention, can be evaporated during the oxidation process. Suitable thiol compounds to be oxidized by this invention include, but are not limited to benzenethiols, such as ethylbenzenethiols and phenylpropanethiols; toluenethiols, such as tolylbutanethiols; xylenethiols, such as xylylpentanethiols; straight chain and branched octanethiols, nonanethiols, decanethiols, undecanethiols, dodecanethiols, tridecanethiols, tetradecanethiols, pentadecanethiols, dexadecanethiols, heptadecanethiols, and octandecanethiols; cyclohexanethiols, such as diethylcyclohexanethiol and methylpropylcyclohexanethiol; cyclopentanethiols, such as methylcyclopentanethiols and methylethylcyclopentanethiol; cycloheptanethiols, such as methylpropylheptanethiol and diethylcycloheptanethiol; phenylcyclopentanethiols; phenylcyclohexanethiols; phenylcycloheptanethiols; tolycycloheptanethiols; xylylcycloheptanethiols; and the like.

The reactants can be combined in a reaction zone essentially simultaneously and allowed to react. In one embodiment, the thiol compound is added directly to a reaction vessel, usually before any other reactants, in a quantity sufficient to result in about 50 to about 99 weight percent, after all five reactants are in the reaction vessel. Preferably, the thiol compound concentration is about 85 to about 98 weight percent, and most preferably about 95 to about 97 weight percent, for efficient reagent use, as well as to minimize reaction time.

The oxidant used in this invention can be any oxidant, such as, for example, air, oxygen, a synthetic mixture of oxygen and inert gasses, hydrogen peroxide, and the like. A gaseous oxidant, such as air, is preferred for ease of use and ready availability. The oxidant can be added directly to the reaction vessel or, if a gas, it can be continuously sparged, or bubbled, into the reaction vessel during the course of the reaction.

The addition of the oxidant has a dual effect. Primarily, the oxidant is necessary to commence and maintain the reaction. Additionally, since the reaction is exothermic, the oxidant can be used as one means of temperature control. An increase in the oxidant feed rate or reactor oxidant concentration produces more heat. If the reactor vessel has a separate means for cooling, controlling the oxidant feed rate or reactor oxidant concentration in order to maintain an appropriate reactor temperature is not always necessary.

The oxidant is added in a quantity sufficient to maintain an appropriate reaction temperature, preferably in a continuous manner to maintain an appropriate oxidation rate. For example, if the oxidant is a gas, it can be bubbled into a reaction vessel containing a volume of about 1,000 gallons of reactants at a rate of less than or equal to about 50 standard cubic feet per minute (scfm); preferably in the range of about 3 scfm to about 40 scfm, and most preferably in the range of about 5 scfm to about 25 scfm.

The aqueous base used in this invention can be any metal hydroxide, or combination thereof; however, for ease of use and availability, an alkali metal hydroxide is preferred. Suitable metal hydroxides include, but are not limited to, barium hydroxide, calcium hydroxide, lithium hydroxide, sodium hydroxide, potassium hydroxide, rubidium hydroxide, and cesium hydroxide. Preferably, sodium hydroxide and/or potassium hydroxide are used. To facilitate addition of the metal hydroxide to the reaction vessel, the metal hydroxide can be dissolved in water prior to addition to the reaction vessel.

The metal hydroxide is added to the reaction vessel relative to the quantity of mercaptan compound added. The mole ratio of mercaptan compound to metal hydroxide is in the range of about 40:1 to about 4:1. Preferably, the mole ratio is in the range of about 13:1 to about 5:1. If too much alkali metal hydroxide is added to the reactor, the disulfide product can appear "burned", or dark in color. Some applications for high molecular weight disulfides require a light-colored, or colorless disulfide. One method to quantify color is the Gardner color number, as determined according to ASTM method D1544-80. Any color is acceptable, but preferably, for some applications, the disulfide product has a Gardner color number of less than or equal to about 3. Therefore, the pH of the reaction vessel contents is maintained in the range of about 8 to about 14, preferably in the range of about 10 to about 12, and most preferably at a pH of about 11.

Any divalent transition metal ion can be used to catalyze the thiol compound oxidation reaction. Preferably, at least one compound selected from the group consisting of divalent transition metal carboxylic acid salts and divalent transition metal sulfate salts is used. Transition metals are any elements that have a partly filled "d" or "f" electron shell in any of their commonly occurring oxidation states. The divalent metal ion is usually in the form of a salt. Salts are a class of compounds derived from acids by replacement of part or all of the acid hydrogen by a metal or metal like radical. For example, copper sulfate is a copper salt of sulfuric acid. Suitable divalent metals include, but are not limited to, copper, cobalt, iron, zinc, silver, and chromium. Preferably, copper is used because of ready availability and ease of use. The acids used to form the salts used in this invention include, but are not limited to, carboxylic acids and sulfuric acid. Naphthenic acids are just one example of a suitable carboxylic acid. Naphthenic acids are any of a group of saturated fatty acids derived from the gas-oil fraction of petroleum by extraction with a caustic soda solution and subsequent acidification. Gulf and West coast crude oils are relatively high in naphthenic acids. The main distinguishing structural feature of naphthenic acids is a hydrocarbon chain consisting of single or fused cyclopentane rings, which are alkylated in various positions with short aliphatic groups. Metal naphthenates contain a metal atom, M, in place of the hydrogen atom of the carboxylic acid functional group. FIG. 1, below, represents a general structure of metal naphthenates.

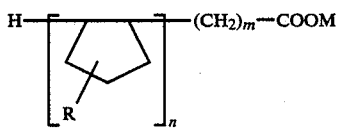

(FIG. 1)

Examples of divalent copper salts include, but are not limited to, copper sulfate and copper napthenate; copper sulfate is especially preferred.

The divalent metal metal ion can be added to the reaction vessel as a solid, or in a liquid form. Sufficient divalent metal ion is added to the reaction vessel to produce an initial reaction vessel concentration in the range of about 50 to about 1000 milligrams per liter (mg/L). The concentration of the divalent metal affects both the oxidation reaction time and the product purification procedure. A higher divalent metal concentration will result in a shorter oxidation reaction time, but will also result in a disulfide product with a high divalent metal concentration. Conversely, if a lower divalent metal concentration is used, the oxidation reaction will take longer to complete, but a purer disulfide product is produced. Thus, preferably, the divalent metal ion is added to the reaction vessel to result in an initial vessel concentration in the range of a about 100 to about 800 mg/l for maximum oxidation reactivity and minimum purification time.

The thiol compound oxidation is carried out in an organic solvent, or medium, in which the thiol compound, divalent metal ion catalyst, oxidizing agent, aqueous base, and reaction intermediate compounds are at least partially soluble. The organic compounds used as diluents in this invention are normally liquid, water miscible, oxygen-containing organic compounds selected from the group consisting of polyhydric alcohols, and mono- and dialkyl ethers of alkylene glycols. Preferably dialkyl ethers of alkylene glycols are used for best reactant solubility and ease of use.

Exemplary compounds include glycerol, ethylene glycol, diethylene glycol, triethylene glycol, trimethylene glycol, tetramethylene glycol, 1,2-propylene glycol, dipropylene glycol, 1,3-butylene glycol, 1,4-butylene glycol, 1,2,6-hexanetriol, 1,2,4-butanetriol; monomethyl, monoethyl, monobutyl ethers of ethylene glycol, propylene glycol and diethylene glycol; monomethyl and monoethyl ethers of triethylene glycol; dimethyl, diethyl ethers of diethylene glycol, dipropylene glycol, and triethylene glycol; thiodiethylene glycol, and the like, and mixtures thereof. Glycol compounds and their manner of preparation are disclosed in Kirk-Othmer, *Encyclopedia of Chemical Technology*, Third Edition, Vol. 11, pages 933–971.

OXIDATION REACTION CONDITIONS

The oxidation reaction can be carried out using either batch or continuous operation, although the invention is particularly well suited for batch operation. Suitable equipment, such as reaction vessels, tubes, valves, and the like are well known in the art can be employed. No special materials of construction for the reaction vessel are required, so taht steel stainless steel, glass-lined reactors, or the like, can be employed.

The reaction temperature can vary, depending on the thiol compound and oxidant(s) employed. Temperatures of less than or about 55° C. are suitable. Temperatures of about 30° to about 52° C. are preferred with a range of about 38° to about 50° C. most preferred because optimum reaction rates are obtained with a minimum corrosive effect on the reaction vessel and minimum discoloration effect on the reaction product. Pressure during the oxidation reaction can vary. Preferably, for ease of operation, a portion of the reaction vessel is open and the vessel contents are at atmospheric pressure.

The contact time required for the oxidation reaction depends upon several factors, such as temperature, pressure, structure of the reactants employed, level of conversion desired, and the like. The length of time during which the oxidizable thiol compounds are contacted with the reagents can vary conveniently between about one-half day and about 50 days although shorter and longer contact times can be employed. Preferably, times of about one day to about 20 days are employed.

The oxidation reaction is complete when the mercaptan sulfur number, expressed as weight percent mercaptan sulfur, is at or below a predetermined level. The mercaptan sulfur method is based on the reaction of the mercaptan with silver nitrate in a pyridine-isopropyl alcohol solvent, to form a silver mercaptide with the liberation of nitric acid. The pyridine present in the solvent prevents the further reaction of the mercaptide with silver nitrate. The nitric acid liberated in the reaction is titrated with standard sodium hydroxide to an end point indicated using a thymol blue-phenolphthalein indicator.

The mercaptan sulfur number is determined by placing 25 milliliters (mls) of isopropyl alcohol and 15 mls pyridine into a 250 ml Erlenmeyer flask. Between about 0.1 and 1.5 grams (gms) of mercaptan are accurately weighed into the Erlenmeyer flask. Then 0.793 gms silver nitrate, 40 mls distilled water, and 1 ml indicator solution are added to the Erlenmeyer flask. The indicator solution is prepared by mixing 1 volume of 0.5 weight percent thymol blue in a solution of 50 volume percent methyl alcohol and 50 volume percent water, with 3 volumes of 0.5 weight percent phenolphthalein in 50 volume percent methyl alcohol and 50 volume percent water. The contents of the Erlenmeyer flask are titrated to a blue end point with 0.05 Normal sodium hydroxide solution. A blank is also determined by titration of the same amount of reagents in an Erlenmeyer flask without any mercaptan added. The weight percent mercaptan sulfur is determined according to:

$$\frac{(A - B)(K)}{(\text{gms sample})}$$

where:
A = ml of NaOH use for sample
B = ml of NaOH used for blank
K = Mercaptan Sulfur Factor (Normality of NaOH × 3.206 The weight percent mercaptan sulfur usually is at or below about 10 percent. Preferably, the percent mercaptan sulfur is at or below about 1.0 percent and most preferably, at or below about 0.8 percent, for most efficient reactant use and product yield.

PRODUCT PURIFICATION

Upon completion of the oxidation reaction, the disulfide product can be purified to reduce impurities, such as divalent transition metal ions.

For instance, the contents of the reaction vessel can be water washed. Any volume of water is beneficial, but for best results and ease of phase separation, about an equal volume of water is combined with an equal volume of product. Preferably, the water has a temperature in the range of about 30° to about 55° C. A water wash is especially preferred if an acid wash will be used. The water wash dilutes and/or removes the aqueous base prior to the addition of an acid wash. The aqueous and organic phases in the reaction vessel are allowed to separate and the water layer can be drained off.

The organic layer, containing disulfide product, can be washed with an acidic solution. Preferably, for safety and efficient reagent use, the acid wash follows a water wash. Any water soluble acid can be used. Preferably, hydrochloric acid is used for most effective reagent use and most effective divalent transition metal removal. Like the water wash, any temperature is acceptable, but the preferred temperature of the acid solution is in the range of about 30° to about 55° C. Any amount of acid can be beneficial and the amount of acid used for the wash can vary depending on the acid strength or concentration. For example, if hydrochloric acid is used, about a 3 percent by volume of concentrated acid in water can be used. About equal volumes of the 3% acid solution and product are combined. The acid and disulfide solutions can remain combined for any amount of time, however, a time of about 12 hours is usually sufficient. The acid and product can be contacted in any manner. The solutions can merely stand, or, for better purification, a mixer can be used. After an appropriate time, such as, for example, 12 hours, the aqueous and organic phases are allowed to separate. The water/acid layer can be drained off and discarded.

If desired, the disulfide product can be water washed again, as described above, air dried, and filtered into appropriate storage vessels.

The temperature and pressure during this purification step are preferably ambient and atmospheric, respectively. No specific temperature or pressure controls are necessary. Any type of vessel can be used for the product purification. Preferably, a vessel which is inert to acids is used. However, if the acid solution is sufficiently dilute, such as, for example, 3% hydrochloric acid, any type of vessel can be used and minimal corrosion occurs.

EXAMPLES

A further understanding of the present invention and its advantages will be provided by reference to the following examples.

EXAMPLE I

The following reactants, expressed in units of parts by weight, were added to a batch reactor: 800 parts tert-dodecyl mercaptan (available from Phillips 66 Company as Sulfole 120 TM), 7 parts anhydrous copper sulfate, 40 parts 2-(2-methoxyethoxy)ethanol (available from Union Carbide Corporation as Methyl Carbitol TM), and 40 parts 50% by weight sodium hydroxide. Air was sparged into the reactor. The reactor temperature was maintained between about 30° to about 55° C. A mercaptan sulfur number was initially determined and then on each day thereafter. The results of the mercaptan sulfur analyses are shown in Table I.

TABLE I

| Day | Mercaptan sulfur, wt. % |
| --- | --- |
| 0 | 15.7 |
| 1 | 10.0 |
| 2 | 8.3 |
| 3 | 6.7 |
| 4 | 4.8 |
| 5 | 2.9 |
| 5–7 | 2.9 |

After the seventh day, the disulfide product was washed with an equal amount of water four times. The product was then air dried. The yield was about 760 parts by weight of tert-dodecyl disulfide, which, based on the theoretical yield, is about a 94% yield.

This example demonstrates that the oxidation reaction is viable and produces a disulfide product with a good yield.

EXAMPLE 2

Reactants were added to a batch reactor in the following order: (1) tert-dodecyl mercaptan (available from Phillips 66 Company as Sulfole 120 ™); (2) air sparge; (3) copper sulfate pentahydrate; (4) 2-(2-methoxyethoxy)ethanol (available from Union Carbide Corporation as Methyl Carbitol ™); and (5) 50% by weight sodium hydroxide in water. At all times, the temperature was maintained below about 55° C. by changing the air sparge rate and/or using an external water cooling jacket. In run 201, about one third of the sodium hydroxide was added in small aliquots. After the mixture reacted for about 5 days, additional aliquots of sodium hydroxide were added when the mixture temperature got below about 25° C. The reaction was complete in about 16 days.

Run 202 had a continuous mixer started after the air sparge was begun, but before copper sulfate was added. Furthermore, in run 202, all of the sodium hydroxide was added at once and no more was subsequently added. The reaction was complete in about 7 days. The tertiary-dodecyl disulfide produced in run 202 was water washed 3 times with 40° C. water. Water was added in a 1:1 volume ratio with the disulfide product. The organic and aqueous phases were allowed to separate for about 3 hours each water wash. The final, washed disulfide product was filtered through a 25μ filter and analyzed.

Data concerning runs 201 and 202 are in Table II.

TABLE II

|  | Run 201 | Run 202 |
|---|---|---|
| Reactants, approximate parts by weight |  |  |
| Sulfole 120 ™ (t-$C_{12}$SH) | 1600 | 3900 |
| $CuSO_4.5H_2O$ | 20 | 50 |
| Methyl carbitol- (2-(2-methoxyethoxy)ethanol) | 80 | 200 |
| 50% NaOH | 320 | 200 |
| Products, tertiary-dodecyldisulfide, approximate parts by weight |  |  |
| Expected | 1400 | 3900 |
| Actual | ∅* | 3200 |
| Product, tertiary-dodecyldisulfide, analysis |  |  |
| Appearance | dark, "burnt" | yellow orange |
| Mercaptan sulfur, wt. % | 0.03 | 0.3 |
| Gardner color number | 14 | 3 |
| Cu content, mg/L | — | 1600 |

*Problems probably caused by excess NaOH, poor temperature control, and poor mixing This example, again, shows that the oxidation reaction of the invention is viable. It also shows that the physical properties of the resultant disulfide product can be altered by the reactant concentrations and reaction conditions.

EXAMPLE 3

Comparative disulfide production runs were made in a batch reactor. Similar concentrations of tert-dodecylmercaptan (available from Phillips 66 Company as Sulfole 120 ™), 2-(2-methoxyethoxy)ethanol (available from Union Carbide Company as Methyl Carbitol ™), and 50% by weight sodium hydroxide were added to the reactor. Air was sparged into each batch at a similar rate for a similar amount of time. However, different divalent metal compounds and different divalent metal concentrations were used in each run. The results of each run are listed in Table III.

TABLE III

| Run # | Divalent Metal Compound | Divalent Metal conc. in reactor, mg/l | Reaction time, days | Mercaptan sulfur, wt. % |
|---|---|---|---|---|
| 301 | $CuSO_4$ | 100 | 33 | 0.6 |
| 302 | $CuSO_4$ | 200 | 29 | 0.4 |
| 303 | $CuSO_4$ | 1000 | 24 | 0.6 |
| 304 | Copper naphthenate | 100 | 5 | 0.4 |
| 305 | Cobalt naphthenate | 100 | 5 | 0.5 |

Upon completion of run 303, the disulfide product was found to contain about 770 mg/L copper. The product was warm water washed with an equal volume of water with a temperature in the range of about 30° to about 55° C. The organic and aqueous layers were allowed to separate and the aqueous layer was discarded. The product was then washed with an equal volume of a dilute aqueous hydrochloric acid solution, about 3% HCl by volume, with a temperature in the range of about 30° to about 55° C. The mixture was stirred for about 12 hours and allowed to separate. The aqueous layer was discarded. The product was warm water washed again, similar to the first warm water wash. The aqueous layer was discarded. The product was air dried with air sparging, at ambient temperatures, and found to contain about 16 mg/L copper.

This example demonstrates that a higher divalent transition metal concentration increases the reaction rate; the oxidation reaction will go to completion quicker. The example also shows that, if desired, the disulfide product can be further purified under mild conditions.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for producing a disulfide product comprising combining the following reactants:
    (a) at least one compound of the formula R-SH containing from about 8 to about 18 carbon atoms wherein R is selected from the group consisting of alkyl, aryl, aralkyl, alkaryl, cycloalkyl, arylcycloalkyl radicals, and mixtures thereof;
    (b) at least one oxidizing agent in a quantity sufficient to maintain an appropriate reaction temperature and to maintain an appropriate oxidation rate;
    (c) at least one aqueous metal hydroxide base sufficient to give a pH of about 8 to about 14;
    (d) at least one normally liquid oxygen containing, water miscible organic compound selected from the group consisting of polyhydric alcohols, and mono- and dialkyl-ethers of alkylene glycols; and
    (e) at least one compound selected from the group consisting of divalent transition metal carboxylic acid salts, divalent transition metal carboxylic acid derivative salts, and divalent transition metal sulfate salts.

2. A process according to claim 1 wherein said reactants are combined in a vessel substantially simultaneously and allowed to react.

3. A process according to claim 1 wherein said R-SH compound is dodecylmercaptan.

4. A process according to claim 1 wherein said R-SH compound contains about 10 to about 16 carbon atoms per molecule.

5. A process according to claim 1 wherein said R-SH compound is initially present in a reactor vessel in a concentration in the range of about 50 to about 99 weight percent, based on the contents of all reactants in the reaction vessel.

6. A process according to claim 1 wherein said oxidizing agent is selected from the group consisting of air, oxygen, a synthetic mixture of oxygen and an inert gas, hydrogen peroxide, and mixtures thereof.

7. A process according to claim 1 wherein said oxidizing agent is a gas and is added to a reactor vessel at a rate less than or equal to about 50 standard cubic feet per minute 8. A process according to claim 1 wherein said base of said aqueous metal hydroxide base is an alkali metal hydroxide.

9. A process according to claim 8 wherein said alkali metal hydroxide is selected from the group consisting of lithium hydroxide, sodium hydroxide, rubidium hydroxide, cesium hydroxide, and mixtures thereof.

10. A process according to claim 1 wherein said base of said aqueous metal hydroxide base is selected from the group consisting of magnesium hydroxide, calcium hydroxide, barium hydroxide, lithium hydroxide, sodium hydroxide, rubidium hydroxide, cesium hydroxide, and mixtures thereof.

11. A process according to claim 1 wherein said base of said aqueous metal hydroxide base is initially present in a reactor vessel in a mole ratio of said R-SH compound to said aqueous base in the range of about 40:1 to about 4:1.

12. A process according to claim 1 wherein said transition metal is selected from the group consisting of copper, iron, cobalt, zinc, silver, chromium, and mixtures thereof.

13. A process according to claim 1 wherein said divalent metal is initially present in a reactor vessel in a concentration in the range of about 50 to about 1,000 mg/L.

14. A process according to claim 1 wherein said temperature during said reacting step is maintained less than or about 55° C.

15. A process according to claim 1 wherein said pressure during said reacting step is maintained at about atmospheric pressure.

16. A process according to claim 1 further comprising a step of recovering said disulfide product.

17. A process of producing di-tert-dodecyl disulfide comprising combining the following reactants:
 (a) tert-dodecylthiol;
 (b) air;
 (c) sodium hydroxide dissolved in water;
 (d) 2-(2-methoxyethoxy)ethanol; and
 (e) copper sulfate at ambient temperature and pressure.

18. A process according to claim 17 further comprising a step of purifying said disulfide product.

19. A process according to claim 18 wherein said disulfide product is purified with an acidic solution.

20. A process according to claim 19 wherein said acidic solution is an aqueous solution of hydrochloric acid.

21. A process according to claim 20 wherein said aqueous solution of hydrochloric acid is about 3 volume percent of concentrated acid in water.

* * * * *